US005552032A

United States Patent [19]

Xie et al.

[11] Patent Number: 5,552,032
[45] Date of Patent: Sep. 3, 1996

[54] SOLID STATE ION SELECTIVE ELECTRODE AND METHOD OF USING THE SAME

[75] Inventors: Youqin Xie; John N. Harman, III, both of Brea, Calif.

[73] Assignee: Beckman Instruments, Inc., Fullerton, Calif.

[21] Appl. No.: 427,579

[22] Filed: Apr. 24, 1995

[51] Int. Cl.⁶ .................................................. G01N 27/333
[52] U.S. Cl. ........................ 205/789; 204/416; 204/418; 204/419; 205/775; 205/778.5; 205/779; 205/786.5; 205/789.5; 205/792
[58] Field of Search .................................. 204/416, 418, 204/419, 435; 205/775, 778.5, 779, 786.5, 789, 789.5, 792

[56] References Cited

U.S. PATENT DOCUMENTS

| | | | |
|---|---|---|---|
| 3,492,216 | 1/1970 | Riseman et al. | 204/419 |
| 3,562,130 | 2/1971 | Hoole et al. | 204/419 |
| 3,563,874 | 2/1971 | Ross et al. | 204/195 |
| 3,662,745 | 5/1972 | Cosentino | 204/435 |
| 3,672,962 | 6/1972 | Frant et al. | 204/419 |
| 3,700,576 | 10/1972 | Bloch et al. | 204/418 |
| 3,822,198 | 7/1974 | Bauke | 204/419 |
| 3,824,169 | 7/1974 | Vanosch et al. | 204/419 |
| 3,864,233 | 2/1975 | Dietrich et al. | 204/418 |
| 3,926,764 | 12/1975 | Ruzicka et al. | 204/195 F |
| 4,083,764 | 4/1978 | Van de Leest et al. | 204/195 M |
| 4,096,049 | 6/1978 | Van de Leest et al. | 204/195 M |
| 4,303,740 | 12/1981 | Petro et al. | 204/419 |
| 4,431,508 | 2/1984 | Brown, Jr. et al. | 204/418 |
| 4,936,975 | 6/1990 | Shibata et al. | 204/418 |
| 5,011,588 | 4/1991 | Rao et al. | 204/409 |
| 5,013,421 | 5/1991 | Rao et al. | 204/409 |
| 5,032,363 | 7/1991 | Simon et al. | 422/82.03 |
| 5,102,527 | 4/1992 | Shibata et al. | 204/416 |
| 5,112,471 | 5/1992 | Shibata et al. | 204/418 |
| 5,200,053 | 4/1993 | Shimomura et al. | 204/435 |
| 5,273,631 | 12/1993 | Ohsawa et al. | 204/153.13 |
| 5,286,365 | 2/1994 | Shu | 204/418 |
| 5,312,537 | 5/1994 | Harrison et al. | 204/416 |
| 5,344,547 | 9/1994 | Vlasov et al. | 204/419 |

OTHER PUBLICATIONS

Pungor, E., *Analytical Chemistry*, V. 39, No. 13, p. 28A (1967).

*Primary Examiner*—T. Tung
*Attorney, Agent, or Firm*—William H. May; Gary T. Hampson

[57] ABSTRACT

A solid state ion-selective electrode device to detect a selected ion species in solution an electrode consisting of a homogeneous solid mixture. The mixture is a solid electrolyte composition possessing ionic conductivity and polyvinyl chloride, and optionally graphite. The electrode is substantially free of metallic silver. An electrical connection operates as a contact between the electrode device and a reference source. Methods for detecting the selected ion species in solutions, such as biological samples utilizing the above described electrodes, are also disclosed.

30 Claims, 4 Drawing Sheets

SOLID STATE ION SELECTIVE ELECTRODE AND METHOD OF USING THE SAME

BACKGROUND

Ion selective electrodes (ISE's) have widespread applications in the fields of biology, chemistry, and medicine. These electrodes provide a useful analytical technique for detecting and measuring the concentration of a particular ion species in solution. The applications of ISE's are numerous, including biomedical research, clinical testing, industrial pollution testing, and chemical-process control.

In clinical medicine, ISE's are important in the diagnosis and treatment of diseases due to their ability to measure ion concentrations in blood, serum, plasma, cerebral spinal fluid, and urine samples. Ions commonly measured in clinical testing include cations and anions. For example, chloride ion levels in bodily fluids are characteristic of certain electrolyte and metabolic disorders including cystic fibrosis, the most common serious genetic disorder in the United States. Similarly, measurements of calcium ion concentration levels are used in the diagnosis of endocrine and renal diseases and in monitoring diseases like cancer. Therefore, it is important that ion concentrations be accurately measured.

Currently, electrolyte analyzers have been developed based on ion-selective electrode technology. In such analyzers, an ISE and an external reference electrode pair are immersed simultaneously in a sample solution. An electrical potential is developed between the electrodes, due to the presence of the ion to which the ISE is sensitive. By measuring this potential, the concentration of the ion can be determined.

Early designs of ISE's comprised an ion selective membrane affixed to the lower opening of a plastic electrode body. The electrode body has an inner electrolyte solution and a reversible internal reference electrode sealed within. This design has several disadvantages including low durability and low reproducibility.

In more recent designs, solid state ion selective electrodes have been developed which utilize a solid ion selective membrane. However, a problem encountered with electrodes of this type is weakness in the physical adhesion between the ion selective membrane and the electrode body. This can alter the membrane potential resulting in inaccurate ion measurements. In addition, electrodes having an internal reference electrode and solution are relatively delicate instruments, thus requiring frequent maintenance.

In order to overcome these problems, solid state ion selective membrane electrodes have been developed which eliminate the inner electrolyte solution and reference electrode. In this type of ISE, the liquid internal reference electrode has been replaced by a solid support which is electrically conductive. These electrodes include a direct electrical contact to the inner surface (the surface not in contact with the sample solution) of the ion selective membrane. The membranes of these electrodes commonly include a polycrystalline pressed pellet of solid electrolytes (made by compressing the solid electrolyte mixture at very high pressures). Additionally, these electrodes may have a silver or gold plating on the membrane inner surface for electrical contact to a voltmeter.

However, a disadvantage associated with these solid state electrodes is the difficulty in providing good physical contact between the ion selective membrane and the element to insure a direct electrochemical interaction. Without a sufficient interaction, variations can occur in the potential difference between the sample and the standard reference electrode resulting in inaccurate and inconsistent ion concentration measurements. Additionally, these types of electrodes tend to drift. Another disadvantage is the deterioration of the ion selective material resulting in the life of the electrode being shortened.

Conventional silver/silver chloride electrodes are commonly used to measure chloride ion concentrations. However, these electrodes have a variety of problems. One problem is that silver/silver chloride electrodes require frequent maintenance such as polishing and bleach cleaning, especially when these electrodes are exposed to many urine samples. Without such maintenance, these electrodes respond sluggishly and are a major cause of reference drifts. Additionally, inconsistencies in electrode performance can be attributed to variability in particle size of the metallic silver powder used to manufacture these electrodes.

For the foregoing reasons, there is a need for an all solid state ion selective electrode which exhibits high selectivity, excellent reliability and the ability to accurately detect and measure the concentration of ions in solution. Further, it would be advantageous for this ion selective electrode to have low impedance, be fast and stable in response to potential, and be able to maintain its performance for prolonged periods of time.

SUMMARY

The present invention is directed to a solid state ion-selective electrode device that meets these needs. The device is used to detect a selected ion species in solution. The device comprises an electrode that is a homogeneous solid mixture of a (i) solid electrolyte composition possessing ionic conductivity and (ii) polyvinyl chloride. The electrode is substantially free of metallic silver, and has an electrical contact which also functions as a reference.

The electrolyte's composition comprises a compound of the selected ion species, and is selective towards a specific ion in solution. The electrolyte composition includes a silver-containing sparingly soluble compound which can be a silver halide selected from the group consisting of silver chloride, silver iodide, and silver bromide. Generally, the homogeneous solid mixture formulation of the electrode is from about 96% to about 99.5% silver chloride and from about 0.5% to about 4% polyvinyl chloride.

A preferable formulation of the homogeneous mixture is about 98% silver chloride and about 2% polyvinyl chloride. All percentages herein are by weight unless stated otherwise.

Optionally, the homogeneous solid mixture can include graphite in the formulation to overcome drawbacks associated with poor electrode performance such as high impedance and slow response to potential. Graphite decreases the porosity of the electrode and acts as a binder for silver chloride, thus prolonging the usable life of an electrode. Generally, the homogeneous solid mixture formulation with graphite included is from about 95% to about 99.5% silver chloride, from about 0.5% to about 4% polyvinyl chloride, and from about 0.1% to about 1% graphite. A preferred formulation of this homogeneous mixture with graphite included is about 97% silver chloride, about 2.5% polyvinyl chloride, and about 0.5% graphite.

A method to detect an ion species in a sample of an aqueous solution, such as a biological fluid using the above-described electrodes, is also disclosed. This method involves contacting the sample with the above-described electrode device, measuring a potential difference between the electrode and a reference source, and detecting the selected ion species in solution.

DESCRIPTION OF THE DRAWINGS

These and other features, aspects, and advantages of the present invention will become better understood with reference to the following description, appended claims, and accompanying drawings where:

DESCRIPTION

According to one aspect of the present invention, there is provided a solid state ion selective device for the detection of a selected ion species in solution which is sensitive, selective, and suitable for analytical use.

Figure 1:
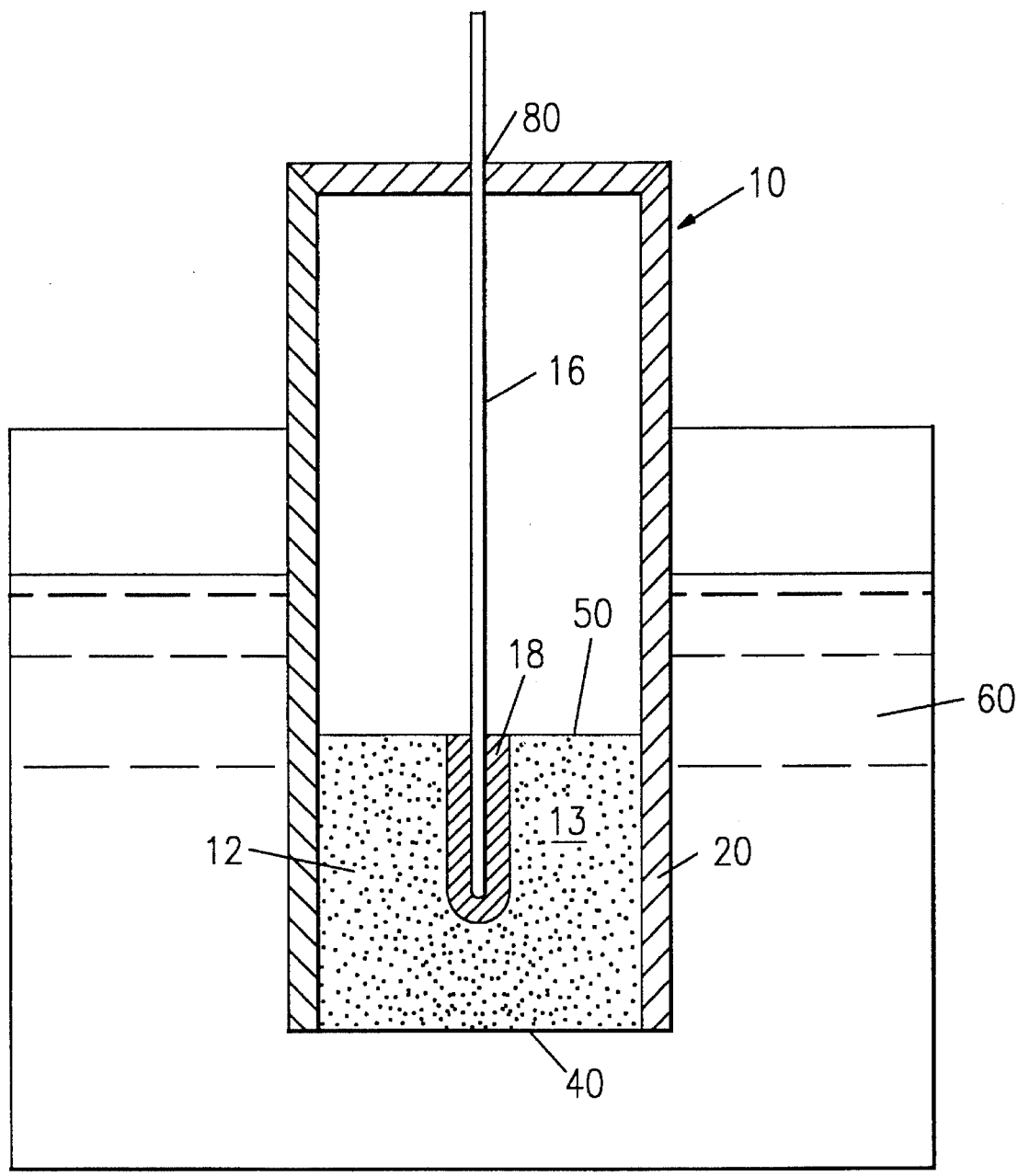
FIG. 1 is a cross sectional schematic view of a solid state ion selective electrode device according to the present invention.

As shown in FIG. 1, the device 10 comprises an electrode 12 having a homogeneous mixture 13, and an electrical connection 16 to the electrode. The mixture comprises a solid electrolyte composition possessing ionic conductivity and polyvinyl chloride. The electrode 12 is substantially free of metallic silver. The electrical connection 16 operates as a contact between the device 10 and a reference source, not shown.

The device 10 can be placed in an elongated hollow cylindrical housing 20 for protection and convenience of use. The housing 20 is made of any suitable material that is substantially chemically inert to the sample solution being tested. For example, a plastic, such as polyvinyl chloride, glass, or a ceramic can be used. Other suitable materials are known to those skilled in the art.

The electrode 12 provides a pair of exposed faces, first 40 and second 50 faces. The electrode 12 has a diameter which fits snugly within the confines of the housing 20. The first exposed face 40 of the electrode 12 is usually positioned within the housing 20 such that the peripheral surface of the first face 40 is adjacent to the lower edge of the open bottom of 20. In this manner, a substantial portion of the first exposed face 40 can be in direct contact with a sample solution 60.

The first exposed face 40 is relatively flat and planar for contact with the sample solution 60. The second surface 50 is relatively flat and planar. The electrical connection 16 is placed half-way inside the pellet and in contact with the second exposed face 50. The electrical connection 16 extends through an aperture 80 in the closed top of the housing 20 for connection to a reference source.

I. THE ION SELECTIVE ELECTRODE DEVICE

The device 10 is of suitable length and diameter for insertion into the sample solution 60 from about 0.1 mL to about 10 mL. Typically, the device 10 is about 5 mm in diameter. The length of the electrode device can be from about 6 mm to about 15 cm long. Typically, it is from about 6 mm to about 10 mm.

A. The Electrode

The electrode 12 is typically a solid pellet of compressed uniform polycrystalline material. The electrode 12 is preferably substantially free of metallic silver because metallic silver has several properties which contribute to poor electrode performance. The electrode 12 is formed of a homogeneous mixture 13 which comprises (a) a solid electrolyte composition and (b) polyvinyl chloride.

1. The Solid Electrolyte Composition

The solid electrolyte composition is typically a polycrystalline pressed pellet of solid electrolytes. The electrolyte composition possesses ionic conductivity and is selective towards a specific ion in the solution. The ion can be a cation or an anion. The electrolyte composition is chosen according to the ion intended to be measured. The composition can be selective towards a variety of ions including chloride ions ($Cl^-$), bromide ions ($Br^-$), iodide ions ($I^-$), sulfide ions ($S^{-2}$), copper ions ($Cu^{+2}$), cadmium ions ($Cd^{+2}$), mercuric ions ($Hg^{+2}$), and silver ions ($Ag^+$). Table I lists ions to be detected on an electrolyte composition for detecting the ion.

TABLE I

| IONS TO BE DETECTED | ELECTROLYTE COMPOSITIONS |
| --- | --- |
| $Cl^-$ | silver chloride (AgCl) |
| $Br^-$ | silver bromide (AgBr) |
| $I^-$ | silver iodide (AgI) |
| $S^{-2}$ | silver sulfide ($Ag_2S$) |
| $Cu^{-2}$ | copper sulfide (CuS) |
| $Cd^{+2}$ | cadmium sulfide (CdS) |
| $Hg^{+2}$ | mercuric sulfide (HgS) |
| $Ag^+$ | silver chloride (AgCl) |

For the detection of halide ions, the electrolyte composition typically is a silver-containing compound wherein the electrolyte composition includes silver in the form of a silver halide, including silver chloride, silver iodide or silver bromide. Preferably, the electrolyte composition is silver chloride for the detection of chloride ions.

The solid electrolyte composition is preferably a particulate having a particle size capable of maintaining a uniform homogeneous composition when mixed with polyvinyl chloride. A preferred particle size is from about 40 μm to about 100 μm. Larger particle sizes can result in electrode pellets containing uneven patches of solid electrode compositions resulting in poor electrode performance. Most preferably, when silver chloride is chosen for the composition, the size is about 60 μm.

2. Polyvinyl Chloride

Polyvinyl chloride (PVC) is a plastic used to maintain the hydrophobicity of the electrode. Preferably, high molecular weight PVC is used. The molecular weight of the PVC is usually at least 50,000 daltons (weight average). More preferably, the PVC molecular weight is 100,000 daltons.

In a less preferred alternative, the PVC is replaced by another polymer, such as, but not limited to, silicone rubber, Teflon, a polyacrylate polymer, cellulose acetate or any other polymer known to the art.

3. Graphite

Optionally, graphite can be included in the homogeneous mixture 13. Graphite decreases the porosity of the electrode and acts as a binder for the solid electrolyte composition.

Graphite is preferably used as a powder with sizes from about 1 μm to about 10 μm. More preferably, the graphite size is 5 μm.

4. Proportion of Ingredients

The amounts of the solid electrolyte composition and PVC are chosen to maintain an electrode with low impedance, decreased hydrophilicity and porosity without compromising electrode performance.

The amount of solid electrolyte composition used in the homogeneous mixture 13 is preferably from about 96% to about 99.5%. When graphite is included in the homogeneous mixture 13, the amount of solid electrolyte composition is preferably from about 95% to about 99.5%. Solid electrolyte compositions in the amount of 100% are generally more porous and soluble in aqueous solutions. These properties may contribute to a decrease in electrode performance.

The amount of PVC used in the electrode formulation is preferably from about 0.5% to about 4%. At least 0.5% is needed to maintain the hydrophobicity of the membrane. Greater than 4% PVC may contribute to an electrode with slow response. More preferably 2% PVC is used in the electrode formulation.

The amount of graphite used in the electrode formulation is important in eliminating interferences from redox coupling reactions. The amount of graphite is typically at least 0.1%. Preferably the amount of graphite use is from about 0.1% to about 1%. More preferably, the amount of graphite used is 0.5%. Greater than 1% graphite can enhance the conductivity properties of the electrode leading to potential ion selectivity problems.

A preferred formula for a chloride ion selective electrode is:

| | |
|---|---|
| Silver chloride (AgCl) | 98% |
| Polyvinyl chloride (PVC) | 2% |

A preferred formula for a chloride ion selective electrode including graphite in the formulation is:

| | |
|---|---|
| Silver chloride (AgCl) | 97% |
| Polyvinyl chloride (PVC) | 2.5% |
| Graphite | 0.5% |

B. Electrical Connection

The electrical connection 16 operates as a contact between the electrode device 10 and a reference source. The electrical connection 16 can be a wire. The wire can comprise any electronic conductive material, and typically is selected from the group consisting of silver, copper, or gold. Preferably, as shown at 18, the wire is coated with silver chloride (by dipping into a molten silver chloride). Using silver chloride coated silver wires as the electrical connection provides stable half-cell potential and thus reduced electrode drifts.

II. MANUFACTURE OF THE ION SELECTIVE ELECTRODE DEVICE

A process of manufacturing an electrode according to the present invention is as follows:

A pre-determined amount of the homogeneous mixture 13 composition is dispersed into a die mold or any mold commercially available. The electrical connection 16 can be coated as shown at 18 with molten silver chloride and annealed to ensure electrode stability. This connection 16 can then be inserted half-way into the mold. The electrode 12 pellet is formed by pressing the mixture under a pressure of 42,000 to 45,000 psi. The dimensions of the pellet are preferably 5 mm in diameter and 5 mm in length. A connector cable leading to a reference source is typically sealed to the electrical connection. This sealing can be accomplished by soldering, epoxy resin or a conducting sealing compound. The electrode 12 pellet can be placed into a housing 20 of polyvinyl chloride and is typically sealed by epoxy.

The exposing of a clean lower exposed surface 40 of the electrode is preferably done by sanding, most preferably with 600 grit sandpaper. The electrode 12 can be coated with a layer of silicone grease to provide another hydrophobic layer. The ion selective electrode device 10 can then be used.

In some applications, it is desirable to impregnate silicone oil into the electrode to increase electrode stability. This can be accomplished by soaking the electrode device 10 in silicone oil under vacuum conditions for about 30 minutes.

For example, when the ion chosen to be detected is $Cl^-$, the solid electrolyte composition can be AgCl. The silver chloride can be obtained commercially. Preferably, the AgCl is prepared according to the following procedure. Silver chloride is typically synthesized by adding sodium chloride solution into silver nitrate solution under vigorous stirring with excess sodium chloride, forming a silver-chloride deposit. The deposit is first washed thoroughly with water, then with acetone, and dried in a 45° C. vacuum oven overnight. The dried silver chloride is then sifted through 62 μm Nylon sieve. To manufacture the electrode 12 pellet, which can include graphite optionally, the appropriate amounts of silver chloride, graphite (5 μm size) and high molecular weight polyvinyl chloride (PVC, 250 μm size) powders are thoroughly mixed together uniformly. The mixing can either be accomplished by an automatic mixer or by hand. Graphite and PVC powders are commercial products. This mixture is then pressed together following the above described procedures. A cross section of the electrode produced by this method, reveals a uniform homogeneous mixture 13 of silver chloride and polyvinyl chloride.

III. USE OF THE ION SELECTIVE ELECTRODE

Typically, the solid state ion selective electrode devices just described, can be immersed into a sample solution of unknown ion concentration. A standard reference electrode is also placed in contact with the sample solution. The voltage of the electrode device can be measured with respect to the external reference electrode. For example, both the electrode device and the reference electrode can be connected electrically to a reference source such as a potentiometer or voltmeter, to display the voltage or potential difference in millivolts (mV) or concentration units of the ion being measured. In some applications, it is desirable to deproteinize the sample, as proteins or lipoproteins may coat the electrode, interfering with the measurement.

In order that the present invention may be more fully understood, the following Examples and comparative results are given by way of illustration only.

EXAMPLES

Serum samples were either obtained from Interstate Blood Bank or collected from hospitals. Urine samples were collected from Beckman employees. Aqueous standards and Beckman Synchron™ serum controls were used to confirm electrode performance.

Generally, the following chloride electrodes were tested on a Beckman Synchron CX3® analyzer used to detect Cl⁻, and the test results were compared to results obtained on a Beckman Synchron AS® analyzer. The Beckman Synchron AS® employs a coulometric titration method for chloride determination which is considered as a reference method (incorporated by reference "Operating and Service Instructions—Synchron CX3" System"—Beckman Instruments, Inc.).

Serum and urine sample exposures of the chloride electrodes were performed in a test fixture of these analyzers. The fixture consists of a flow cell in which electrodes can be installed, a peristaltic pump, and a controller. A sample solution and buffer solution (containing no samples) were pumped through the flow cell alternatively. Each solution resided in the flow cell for approximately 20 seconds. The serum and urine samples were diluted 20 times using a Synchron CX3 Electrolyte Buffer solution (pH7). The electrodes were removed from the test fixture after it had been exposed to various amounts of serum and urine samples and installed on a Synchron CX3 instrument. The electrodes were then used to measure Cl⁻ concentrations in serum and urine samples. The electrodes were not cleaned between exposures to different samples.

EXAMPLE I: SERUM AND CONTROL CHLORIDE RECOVERY ON SYNCHRON CX3, ELECTRODE STABILITY

Six chloride selective electrodes were prepared according to one aspect of the present invention. Three of the electrodes were prepared with 97.5% silver chloride (AgCl) and 2.5% polyvinyl chloride (PVC) composition (Formula A). The other three electrodes were prepared with 97% silver chloride, 2.5% polyvinyl chloride and 0.5% graphite (Formula B).

A Beckman Synchron CX3® analyzer was used in the test. The Synchron CX3 has control electrodes used to detect Cl⁻ ion concentration made of 40% silver (Ag) and 60% silver chloride.

During the course of instrument testing, electrodes were exposed to serum and cysteine-spiked (10 mg/ml) urine pools to accelerate electrode failure. Chloride ion measurements were taken before exposure to any serum and urine samples. These results are shown in Table 1. After exposure to a total of 13,400 serum and urine samples, chloride ion concentrations for the same samples were again measured. These results are also listed in Table 1.

The results listed in Table 1 represent the averages of two control electrodes, three Formula A electrodes, and three Formula B electrodes. The chloride recoveries for Synchron Control L3 and Serum Pool were also obtained by a Beckman Sychron-AS® analyzer which is considered as the referenced method. The results show that Formula A and Formula B electrodes recover chloride ions on the average of 2 mmol/L to 5 mmol/L lower than that of control Ag/AgCl electrodes. The results also show that Formula A and Formula B electrodes correlate more favorably to Sychron AS® than control electrodes. These results indicate that Formula A and Formula B electrodes are more stable with time as indicated by the smaller change in Cl⁻ recovery after the electrodes have been exposed to various amounts of samples. Thus, these electrodes are less susceptible to serum and urine fouling compared to the control electrodes.

EXAMPLE II: ELECTRODE RESPONSE CURVES AND TIMES

An important characteristic of an ion selective electrode is how fast an electrode responds to changes in ion concentrations, and the stability of the potential outputs. The electrodes and analyzer of Example 1 were used.

Figure 2:
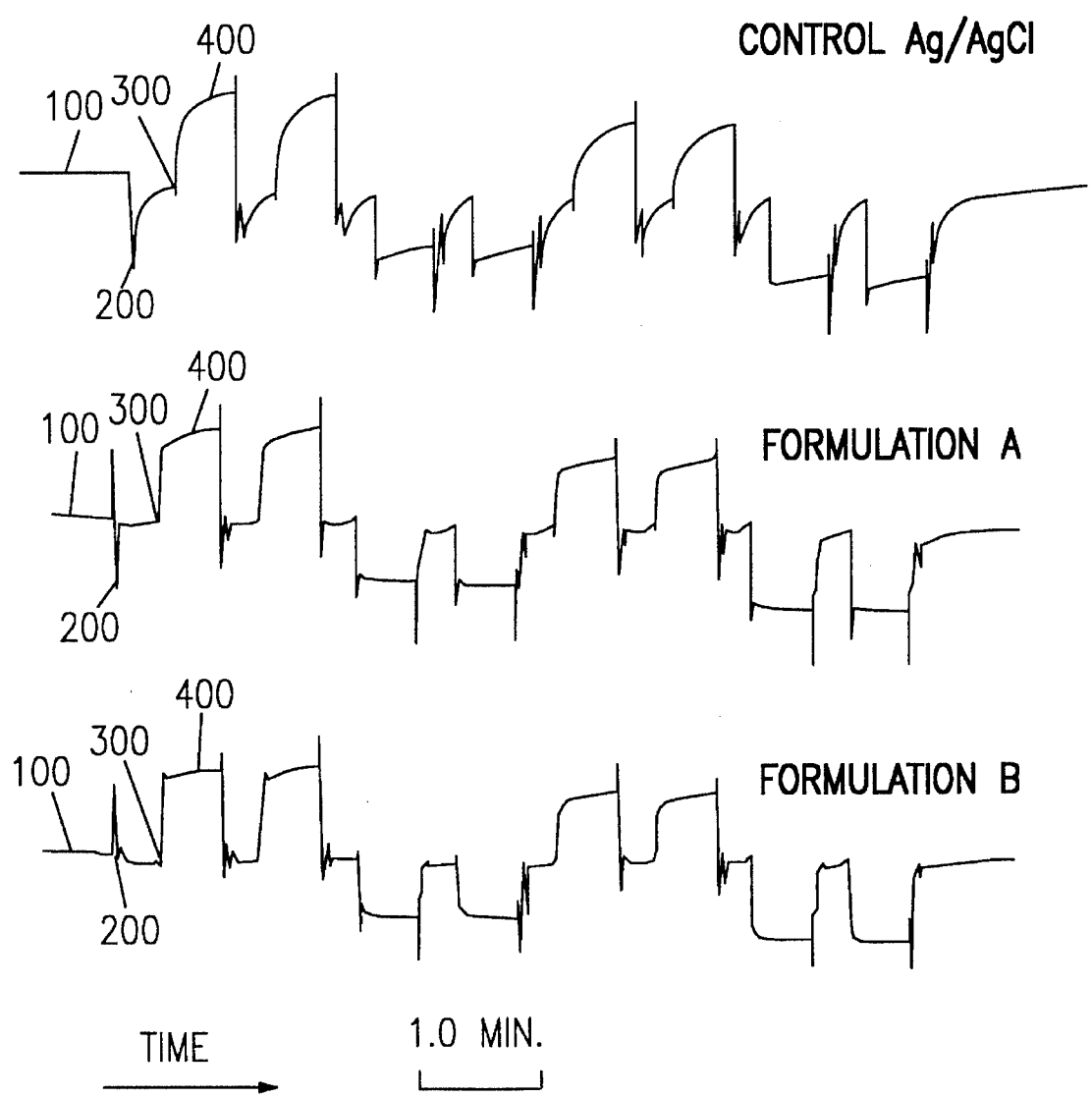
FIG. 2 is a diagram showing a comparison of chloride ion electrode response curves between solid state ion selective electrode devices, according to the present invention, and control silver/silver chloride electrodes.

After electrodes had been exposed to 3,800 serum and urine samples, electrode response curves to Cl⁻ concentration changes were recorded. The results are shown in FIG. 2. Referring to FIG. 2, the electrodes were first exposed to a concentration of reference solution to establish a stable baseline 100. After the baseline was established, the electrodes were then exposed to a sample solution of the same concentration 200. Next, the electrodes were exposed to a sample solution of a different concentration 300. Electrode response curves 400 to changes in sample concentrations were monitored. The control Ag/AgCl electrodes responded slower to changes in sample concentration. In comparison, Formula A and Formula B electrodes exhibited faster responses to changes in concentrations as seen by the flatter curve 400 which does not show any significant tailing. Formula A and Formula B electrodes exhibit faster responses and more stable potential outputs than the control Ag/AgCl electrodes.

TABLE I

Comparison of Chloride Recoveries for Synchron Control and Serum Pool with Control Ag/AgCl and the Silver Metal Free Electrodes Before and After Serum/Urine Exposure

| Electrode Type | Before Exposure to Any Serum & Urine Samples | | After Exposed to Total of 13,400 Serum & Urine Samples | |
|---|---|---|---|---|
| | Synchron Control L3 (mmol/L) | Serum Pool (mmol/L) | Synchron Control L3 (mmol/L) | Serum Pool (mmol/L) |
| Control | 123.4 | 107.3 | 128.9 | 112.5 |
| Formula A | 121.9 | 106.6 | 122.7 | 107.0 |
| Formula B | 121.7 | 106.2 | 123.6 | 108.3 |

NOTE:
1. Control electrodes contain a 40% Ag/60% AgCl
2. Formula A is 97.5% AgCl/2.5 % PVC
3. Formula B is 97% AgCl/2.5% PVC/0.5% Graphite
4. The recoveries of Synchron Control L3 and Serum Pool obtained by Beckman AS ® were 120.8 mmol, and 106.0 mmol/L, respectively.

EXAMPLE III: PATIENT SERUM CHLORIDE RECOVERY ON SYNCHRON CX3

Coulometric titration (Beckman Synchron AS®) for chloride measurement is generally considered as the reference method. It is important that the ion selective electrode method is comparable to the reference method with minimal recovery bias.

Figure 3:
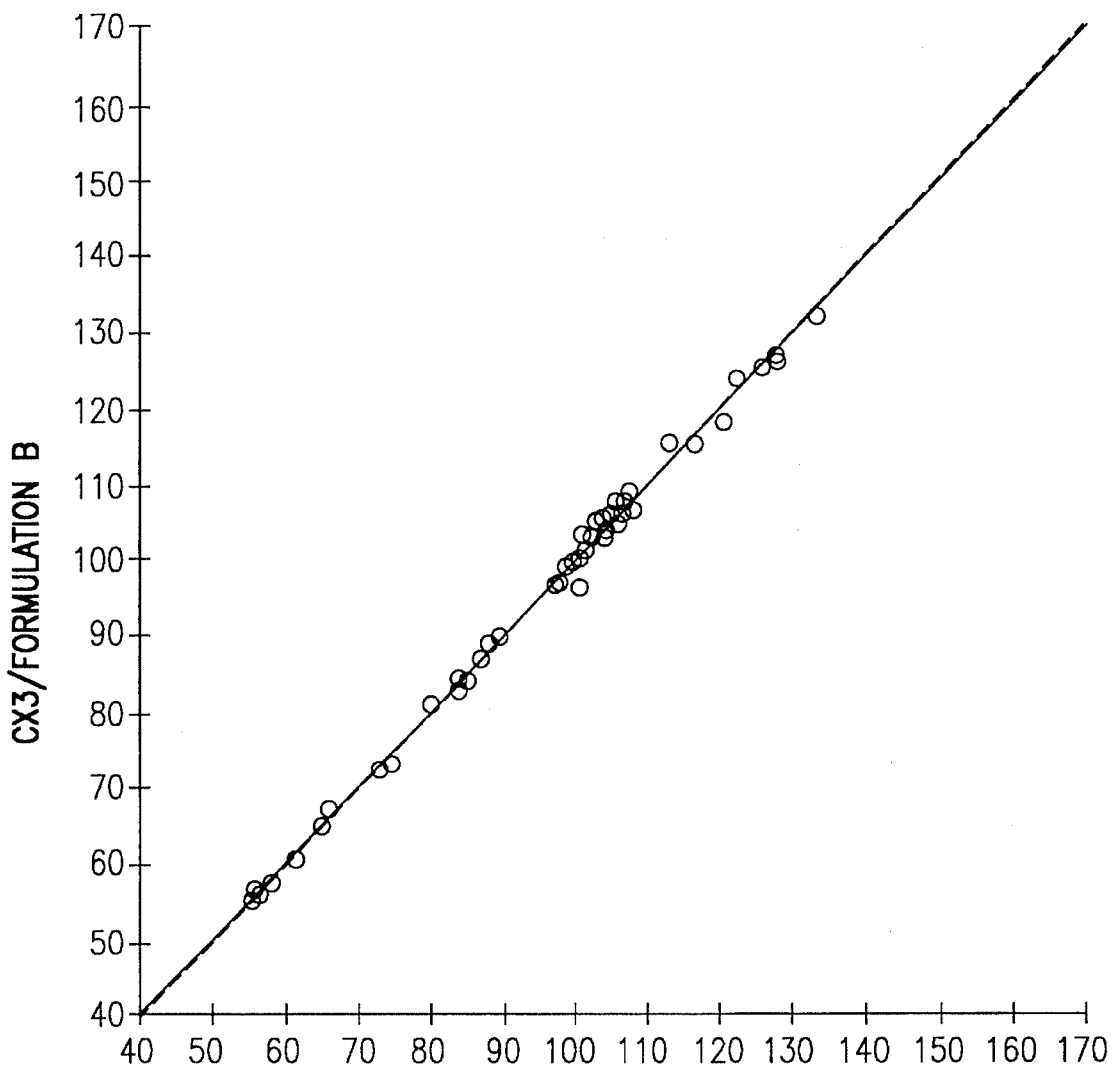
FIG. 3 is a graph showing serum correlation between Beckman CX3/Formulation B Chloride Electrode and Beckman AS® Reference Method.
Figure 4:
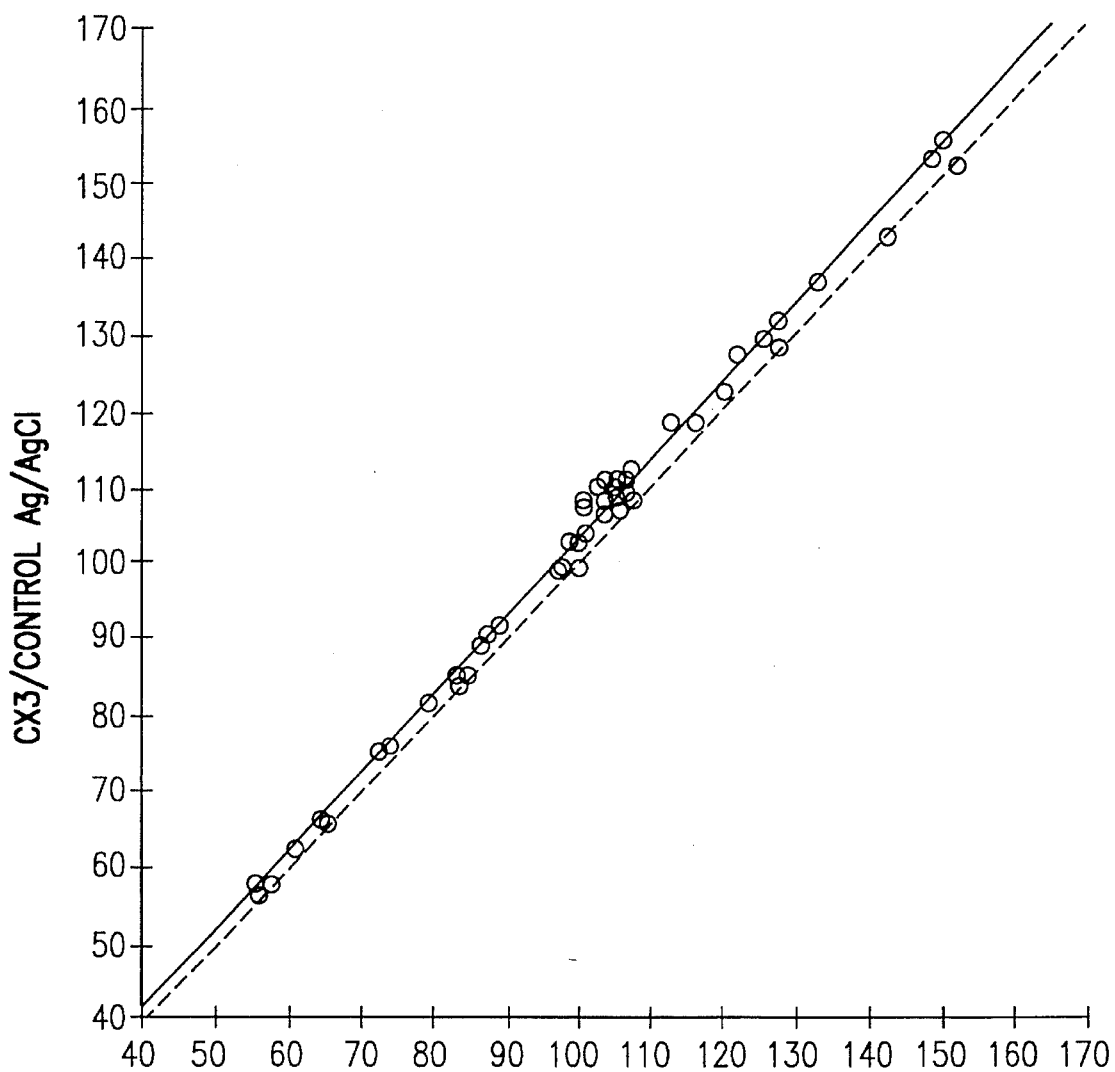
FIG. 4 is a graph showing serum correlation between Beckman CX3/Control Ag/AgCl Chloride Electrode and Beckman AS® Reference Method.

Serum samples were obtained from patients and analyzed for chloride concentrations on two Synchron CX3® instruments which were installed with a Formula B chloride electrode and a control Ag/AgCl electrode respectively. These same samples were also measured on a Synchron AS® analyzer. Results obtained on the Synchron CX3® instruments were then compared to that obtained on the Synchron AS® analyzer as shown in FIGS. 3 and 4. It is clear that the Formula B electrodes recovered serum chloride concentration essentially identical to the coulometric titration method (as indicated by the regression line, FIG. 3). This represents a significant improvement over the control Ag/AgCl electrodes (FIG. 4). One of the major disadvantages associated with conventional Ag/AgCl electrodes is the chloride recoveries are higher than those values obtained by the reference method (i.e., the coulometric method). This high serum bias has been observed by the College of American Pathologists (CAP) surveys. The results shown in FIGS. 3–4 show the improvement of Formula B electrodes as compared to conventional Ag/AgCl electrodes, with regard to this CAP survey.

The present invention provides a solid state ion selective electrode of improved sensitivity and selectivity. In particular, these metallic silver free chloride electrodes offer a number of advantages in comparison to conventional silver/silver chloride electrodes. These electrodes are accurate in detecting and measuring the concentration of ions in solution as indicated by the much reduced Cl⁻ recovery bias (Table 1). Preferably, these electrodes are particularly suited for measurement of chloride ions, but can be used for measurement of other ions. These electrodes have low impedance, fast and stable responses to potential, and are less susceptible to serum and urine fouling. In addition, the composition of the electrode as a solid homogenous mixture with a direct electrical connection to a reference source, bypassing the problems associated with inadequate membrane seals. These types of metallic silver free electrodes are low maintenance and exhibit high performance for prolonged periods of time.

Although the present invention has been described in considerable detail with reference to certain preferred versions, other versions are possible. Thus, the spirit and the scope of the appended claims should not be limited to the description of the preferred versions contained herein.

What is claimed is:

1. A solid state ion selective electrode device for the detection of a selected ion species in solution, the device comprising:
   a) a solid state ion selective electrode consisting essentially of a homogeneous solid mixture comprising (i) a solid electrolyte composition possessing ionic conductivity and (ii) polyvinyl chloride, wherein the electrode is substantially free of metallic silver, the electrode containing sufficient electrolyte composition for detecting the selected ion species in solution and containing no greater than about 4% polyvinyl chloride; and
   b) an electrical connection to the electrode, the connection operating as a contact between the electrode device and a reference source.

2. The device as defined in claim 1, wherein the electrolyte composition comprises a compound of the selected ion species.

3. The device as defined in claim 1, wherein the electrolyte composition is selective towards a specific ion in the solution.

4. The device as defined in claim 3, wherein the electrolyte composition includes a silver-containing compound.

5. The device as defined in claim 4, wherein the silver-containing compound is a silver halide.

6. The device as defined in claim 5, wherein the silver halide is selected from the group consisting of silver chloride, silver iodide, and silver bromide.

7. The device as defined in claim 6, wherein the silver halide is silver chloride.

8. The device as defined in claim 7, wherein the homogeneous mixture of the electrode comprises from about 96% to about 99.5% silver chloride and at least about 0.5% polyvinyl chloride.

9. The device as defined in claim 8, wherein the homogeneous solid mixture of the electrode comprises about 98% silver chloride and about 2% polyvinyl chloride.

10. The device as defined in claim 1, wherein the electrical connection is a wire comprising an electrically conductive material selected from the group consisting of silver, gold and copper.

11. The device as defined in claim 10, wherein the wire is coated with silver chloride.

12. A method of detecting an ion species in a sample of an aqueous solution comprising:
   a) contacting the sample with the device of claim 1;
   b) measuring a difference in electrical potential between the electrode and a reference source; and
   c) detecting the selected ion species in solution.

13. The device as defined in claim 1, wherein the mixture comprises graphite.

14. The device as defined in claim 13, wherein the mixture contains from about 0.1% to about 1% graphite.

15. A solid state ion selective device for the detection of chloride or silver ion species in solution, the device comprising:
   a) a solid state ion selective electrode consisting essentially of a homogeneous solid mixture of (i) about 98% silver chloride, and (ii) about 2% polyvinyl chloride, wherein, the electrode is substantially free of metallic silver; and
   b) an electrical connection to the electrode, the connection operating as a contact between the electrode device and a reference source.

16. A solid state ion selective electrode device for the detection of a selected ion species in solution, the device comprising:
   a) a solid state ion selective electrode consisting essentially of a homogeneous solid mixture of (i) a solid electrolyte composition possessing ionic conductivity, (ii) polyvinyl chloride, and (iii) graphite in an amount of about 0.1% to about 1%, wherein the electrode is substantially free of metallic silver; and
   b) an electrical connection to the electrode, the connection operating as a contact between the electrode device and a reference source.

17. The device as defined in claim 16, wherein the electrolyte composition is selective toward a specific ion in solution.

18. The device as defined in claim 17, wherein the electrolyte composition includes a silver-containing compound.

19. The device defined in claim 18, wherein the silver-containing compound is a silver halide.

20. The device as defined in claim 19, wherein the silver halide is selected from the group consisting of silver chloride, silver iodide, and silver bromide.

21. The device as defined in claim 20, wherein the silver halide is silver chloride.

22. The device as defined in claim 21, wherein the homogeneous mixture of the electrode comprises from at least about 95% silver chloride, and from about 0.5% to about 4% polyvinyl chloride.

23. The device as defined in claim 22, wherein the homogeneous solid mixture of the electrode comprises about 97% silver chloride, about 2.5% polyvinyl chloride, and about 0.5% graphite.

24. A method of detecting an ion species in a sample of an aqueous solution comprising:
   a) contacting the sample with the device of claim 17;
   b) measuring a difference in electrical potential between the electrode and a reference source; and
   c) detecting the selected ion species in solution.

25. The device as defined in claim 16, wherein the electrical connection is a wire comprising an electrically conductive material selected from the group consisting of silver, gold, and copper.

26. The device as defined in claim 25, wherein the wire is coated with silver chloride.

27. The device as defined in claim 16, wherein the solid mixture contains no more than about 4% polyvinyl chloride.

28. A solid state ion selective electrode device for the detection of a selected ion species in solution, the device comprising:

a) a solid state ion selective electrode formed of a homogeneous solid mixture of (i) about 97% silver chloride, (ii) about 2.5% polyvinyl chloride, and (iii) about 0.5% graphite, wherein the electrode is substantially free of metallic silver; and b) an electrical connection to the electrode, the connection operating as a contact between the electrode device and a reference source.

29. The device as defined in claims 1, 15, 16, or 28 wherein the electrode is a pellet.

30. The device as defined in claim 29, wherein the electrode is formed by compression molding.

* * * * *